United States Patent
Ohishi

(10) Patent No.: US 9,460,500 B2
(45) Date of Patent: Oct. 4, 2016

(54) IMAGE PROCESSING APPARATUS AND IMAGE PROCESSING METHOD

(71) Applicant: TOSHIBA MEDICAL SYSTEMS CORPORATION, Otawara-Shi (JP)

(72) Inventor: Satoru Ohishi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/726,965

(22) Filed: Jun. 1, 2015

(65) Prior Publication Data
US 2015/0339809 A1    Nov. 26, 2015

Related U.S. Application Data

(63) Continuation of application No. PCT/JP2013/082276, filed on Nov. 29, 2013.

(30) Foreign Application Priority Data

Nov. 30, 2012 (JP) .................. 2012-261880
Nov. 29, 2013 (JP) .................. 2013-247618

(51) Int. Cl.
*G06K 9/00* (2006.01)
*G06T 5/50* (2006.01)
(Continued)

(52) U.S. Cl.
CPC .............. *G06T 5/50* (2013.01); *A61B 6/032* (2013.01); *A61B 6/504* (2013.01); *A61B 6/5235* (2013.01);
(Continued)

(58) Field of Classification Search
CPC .......... G06T 5/50; G06T 2207/10081; G06T 2207/10116; G06T 2207/20224; G06T 2207/30004; G06T 7/0016; G06T 7/0024; A61B 6/032; A61B 6/504; A61B 6/5235

USPC ................................. 382/128, 131
See application file for complete search history.

(56) References Cited

U.S. PATENT DOCUMENTS 6,373,920 B1 *  4/2002  Hsieh ............... A61B 6/507
                                              378/8
7,545,965 B2 *  6/2009  Suzuki .............. G06T 5/007
                                              382/128

(Continued)

FOREIGN PATENT DOCUMENTS

JP     2000-217035 A     8/2000
JP     2008-029798 A     2/2008
JP     2010-193975 A     9/2010

OTHER PUBLICATIONS

International Search Report issued Jan. 14, 2014 in PCT/JP2013/082276 filed Nov. 29, 2013.

(Continued)

*Primary Examiner* — Tom Y Lu
(74) *Attorney, Agent, or Firm* — Oblon, McClelland, Maier & Neustadt, L.L.P

(57) ABSTRACT

An image processing apparatus includes a display and processing circuitry. The processing circuitry generates second image data by subtracting first image data before and after contrast enhancement. The processing circuitry removes information indicating a structure from pieces of the second image data to generate third image data. The processing circuitry correct misalignment of the third image data based on characteristics of the shape of the subject represented in at least any one of the first to third image data. The processing circuitry obtains a variation index between the third image data after alignment correction, and generates fourth image data base on the variation index. The processing circuitry displays a medical image based on the fourth image data on the display.

19 Claims, 3 Drawing Sheets

(51) Int. Cl.
*G06T 7/00* (2006.01)
*A61B 6/03* (2006.01)
*A61B 6/00* (2006.01)

(52) U.S. Cl.
CPC ........... *G06T 7/0016* (2013.01); *G06T 7/0024* (2013.01); *G06T 2207/10081* (2013.01); *G06T 2207/10116* (2013.01); *G06T 2207/20224* (2013.01); *G06T 2207/30004* (2013.01)

(56) References Cited

U.S. PATENT DOCUMENTS

| | | | | |
|---|---|---|---|---|
| 8,643,642 | B2* | 2/2014 | Mistretta | A61B 6/4441 345/419 |
| 8,731,262 | B2* | 5/2014 | Rauch | G06T 7/2053 382/130 |
| 2002/0151781 | A1 | 10/2002 | Ohishi et al. | |
| 2002/0156368 | A1 | 10/2002 | Ohishi et al. | |
| 2003/0109779 | A1 | 6/2003 | Ohishi et al. | |
| 2006/0082598 | A1 | 4/2006 | Ohishi et al. | |
| 2009/0074276 | A1* | 3/2009 | Doi | G06K 9/6202 382/130 |
| 2010/0215237 | A1 | 8/2010 | Ohishi | |
| 2013/0172734 | A1* | 7/2013 | Hsieh | A61B 6/032 600/425 |

OTHER PUBLICATIONS

A.S. Ahmed, et al., "C-Arm CT Measurement of Cerebral Blood Volume: An Experimental Study in Canines", American Journal of Neuroradiology, vol. 30, May 2009, pp. 917-922.

* cited by examiner

IMAGE PROCESSING APPARATUS AND IMAGE PROCESSING METHOD

CROSS-REFERENCE TO RELATED APPLICATION

This application is based upon and claims the benefit of priority from Japanese Patent Application Nos. 2012-261880, filed 30 Nov. 2012 and 2013-247618, filed 29 Nov. 2013; the entire contents of which are incorporated herein by reference.

FIELD

Embodiments described herein relate generally to an image processing apparatus and an image processing method.

BACKGROUND

There is a method of calculating the amount of blood flow such as cerebral blood volume (CBV) by using a modality such as an X-ray computed tomography (CT) system or an angio system (an X-ray imaging apparatus). For example, the CBV is calculated based on the profile of CT values obtained by continuous scanning. For another example, the CBV is calculated by using a non-contrast image acquired before the injection of a contrast agent and a contrast image acquired after the injection. Specifically, an image of blood vessels including capillaries is created by removing non-vascular regions such as bones and soft tissues from the difference between the non-contrast image and the contrast image. The generated image is displayed, for example, as a color map.

This method is used to determine the results of procedure, therapy, or treatment for a subject. However, it may sometimes be required to make a different decision according to the state of the subject before a procedure. Besides, the blood flow velocity or the like may vary according to the psychological and physical condition of the subject who is to undergo a procedure or the like. In this case, even if the amount of blood flow is calculated before or after a predetermined event such as a procedure, it may be difficult to determine whether the calculation result is influenced by the predetermined event such as a procedure. For example, even if the CBV is calculated based on an examination result obtained after the predetermined procedure, a viewer of an image may not determine whether a portion, which appears in the image or the like as a result of measurement, emerges after the procedure. In such a case, for example, an affected part or the like that has already existed before the procedure may be mistaken for a newly developed affected part.

DETAILED DESCRIPTION

In general, according to one embodiment, an image processing apparatus includes a subtraction data generator, an analyzer, a registration processor, an image processor, a display, and a display controller. The subtraction data generator generates second image data by subtracting first image data after contrast enhancement from first image data before contrast enhancement. The analyzer removes information corresponds to anatomical structures from a plurality of the second image data to generate third image data. The registration processor corrects the positions of a plurality of the third image data obtained at different timings based on structural information represented on image in at least any one of the first image data, the second image data, and the third image data. The image processor obtains a variation index between the third image data after correcting relative positions, and generates fourth image data base on the variation index. The display controller displays a medical image based on the fourth image data on the display.

Figure 1:
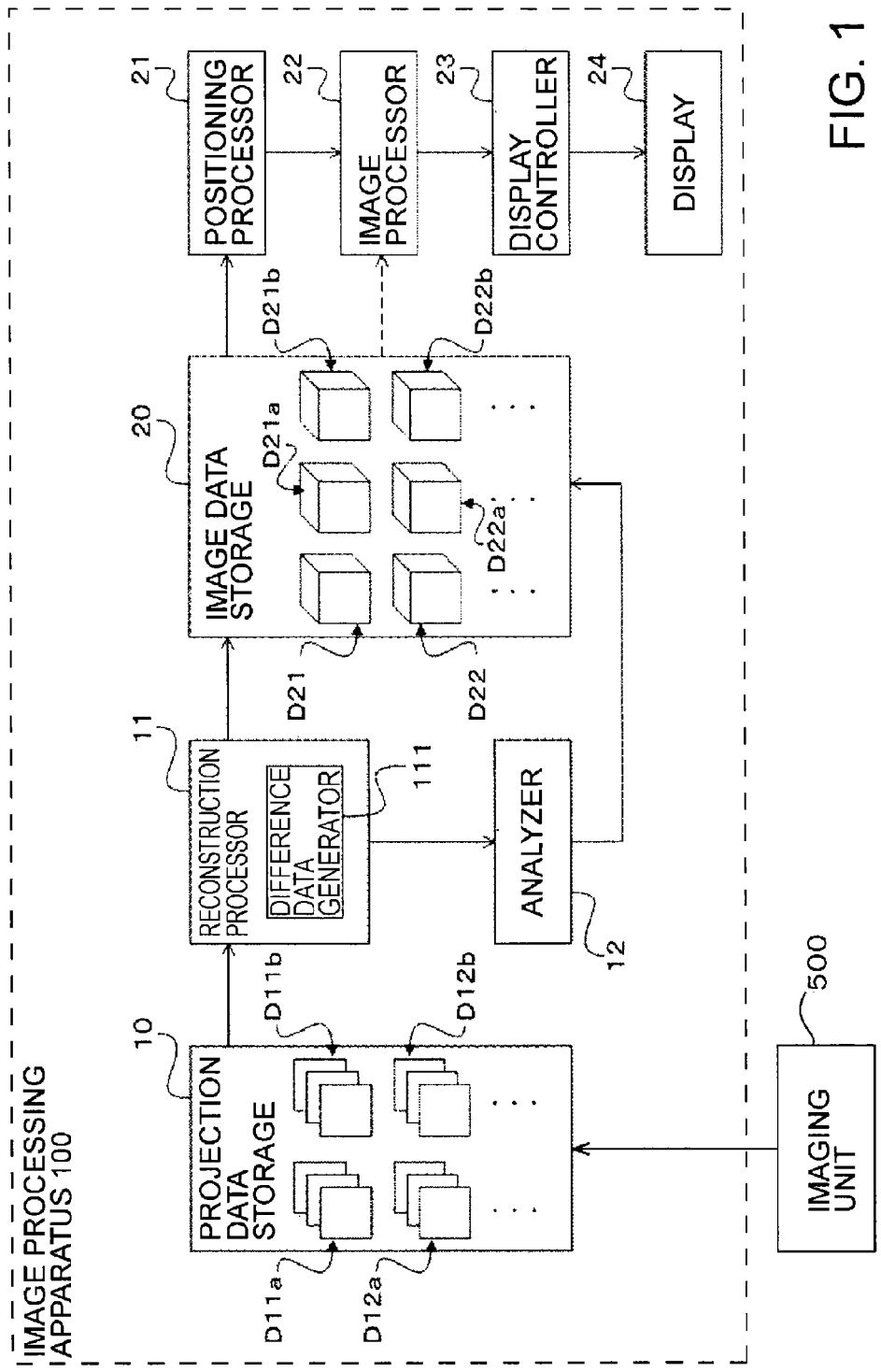
FIG. 1 is a block diagram of an image processing apparatus according to an embodiment.

With reference to FIG. 1, a description is given for a configuration of an image processing apparatus according to an embodiment. As illustrated in FIG. 1, an image processing apparatus 100 of this embodiment includes a projection data storage 10, a reconstruction processor 11, an analyzer 12, an image data storage 20, a registration processor 21, an image processor 22, a display controller 23, and a display 24. As illustrated in FIG. 1, the image processing apparatus 100 of this embodiment receives projection data acquired before and after contrast enhancement by an imaging unit 500. The image processing apparatus 100 generates image data based on the projection data. The imaging unit 500 is a predetermined modality such as an X-ray CT system or an angio system (an X-ray imaging apparatus). The image data is, for example, volume data.

The projection data storage 10 receives projection data acquired at different times by the imaging unit 500. The projection data includes, for example, those obtained prior to a predetermined event (procedure, therapy, or treatment for a subject), and those obtained after the predetermined event. Besides, the projection data can be divided into projection data D11a, D12a, . . . before contrast enhancement and projection data D11b, D12b, . . . after contrast enhancement. The projection data storage 10 stores the projection data in association with examination or treatment information, pre- or post-contrast enhancement, and acquisition time. In the following, let us assume that projection data acquired prior to a predetermined event and projection data acquired after the predetermined event are acquired at different examinations. In addition, the projection data D11a and the projection data D11b are projection data before and after contrast enhancement acquired in the same examination prior to a predetermined event. Similarly, the projection data D12a and the projection data D12b are projection data before and after contrast enhancement acquired in the same examination after the predetermined event. Further, the predetermined event is described as "procedure". Accordingly, hereinafter "procedure" does not always refer to procedure, but may also refer to therapy or treatment for a subject.

The reconstruction processor 11 of the embodiment includes a subtraction data generator 111. In the following, the operation of the reconstruction processor 11 is described first, and then the operation of the subtraction data generator 111 afterward.

The reconstruction processor 11 retrieves projection data, that examination and treatment information, pre- or post-contrast enhancement, and the acquisition time from the projection data storage 10. When the projection data D11a before contrast enhancement and the projection data D11b after contrast enhancement acquired prior to a predetermined event are retrieved, the reconstruction processor 11 performs reconstruction processing after subtracting the projection data D11b from the projection data D11a. Specifically, the reconstruction processor 11 generates image data (tomographic image data or volume data) by a reconstruction algorithm such as Feldkamp algorithm, most famous 3D backprojection algorithm. The reconstruction processor 11 can reconstruct volume data by any method such as three-dimensional Fourier transform, convolution back projection or the like, or cone-beam reconstruction, multi-slice reconstruction, iterative reconstruction, or the like. Hereinafter, image data reconstructed from projection data before contrast enhancement (e.g., the projection data D11a, D12a, . . . ) is sometimes called as "image data before contrast enhancement". Similarly, image data reconstructed from projection data after contrast enhancement (e.g., the projection data D11b, D12b, . . . ) is sometimes called as "image data after contrast enhancement". The image data before and after contrast enhancement correspond to an example of "first image data".

In this manner, the reconstruction processor 11 performs reconstruction processing by using the projection data D11a and the projection data D11b, acquired prior to a procedure, based on predetermined reconstruction conditions. Thereby, the reconstruction processor 11 generates image data D21a before contrast enhancement and image data D21b after contrast enhancement. On the other hand, when the projection data D12a and the projection data D12b, acquired after the procedure, are retrieved, the reconstruction processor 11 performs reconstruction processing by using them, and generates image data D22a before contrast enhancement and image data D22b after contrast enhancement.

The reconstruction processor 11 may perform the reconstruction processing described above according to an instruction from an operator. In this case, the reconstruction processor 11 receives the determination of examination from the operator. The reconstruction processor 11 then retrieves projection data corresponding to the examination and reconstructs it.

The reconstruction processor 11 stores, in the image data storage 20, the image data D21a before contrast enhancement and the image data D21b after contrast enhancement generated prior to a procedure in association with each other. Besides, the reconstruction processor 11 sends the image data D21a and the image data D21b to the subtraction data generator 111. The subtraction data generator 111 generates the subtraction data between these image data.

Figure 2:
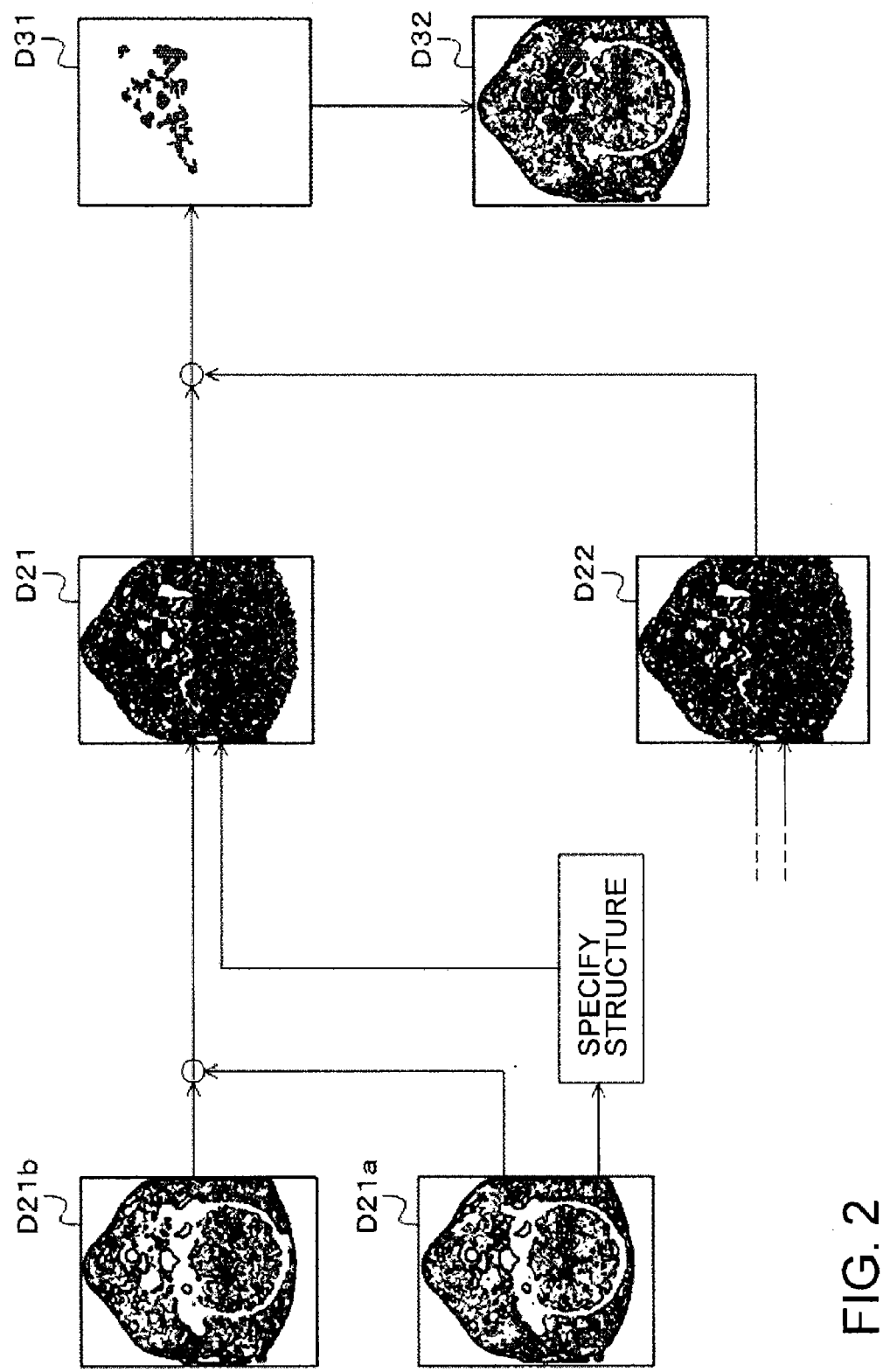
FIG. 2 is a diagram for explaining the outline of the generation and analysis of image data in the embodiment.

Next, referring to FIG. 2, a description is given for processing related to the generation and analysis of image data according to the embodiment. The subtraction data generator 111 generates image data indicating the subtraction data between image data before contrast enhancement and image data after contrast enhancement for each examination (e.g., before and after a procedure). Note that in the following description, the image data indicating the subtraction data is sometimes referred to as "subtraction image data". For example, as illustrated in FIG. 2, the reconstruction processor 11 obtains the subtraction data between the image data D21a before contrast enhancement and the image data D21b after contrast enhancement, where those data were acquired before a procedure. The reconstruction processor 11 then generates first subtraction image data D21. Further, the reconstruction processor 11 obtains the subtraction data between the image data D22a before contrast enhancement and the image data D22b after contrast enhancement, where those data were acquired after the procedure. The reconstruction processor 11 then generates another first subtraction image data D22.

Note that, the subtraction data generator 111 generates subtraction image data based on reconstructed image data at previous example; however, this embodiment is not limited to this. For example, the subtraction data generator 111 may obtain the subtraction data between the projection data D11a before contrast enhancement and the projection data D11b after contrast enhancement, and reconstruct first subtraction image data D21 from subtraction data of projection data. Thus, first subtraction image data is generated by the reconstruction processing. In this case, subtraction image data after a procedure is also generated in the same manner. The subtraction image data generated by any of the above methods corresponds to an example of "second image data".

The subtraction data generator 111 sends any one of or a combination of the first subtraction image data D21 before a procedure, the image data D21a before contrast enhancement, and the image data D21b after contrast enhancement to the analyzer 12. Similarly, the subtraction data generator 111 sends any one of or a combination of the first subtraction image data D22 after the procedure, the image data D22a before contrast enhancement, and the image data D22b after contrast enhancement to the analyzer 12. In the following description, it is assumed that the subtraction data generator 111 sends the first subtraction image data D21 before a procedure, the image data D21a before contrast enhancement, the first subtraction image data D22 after the procedure, and the image data D22a before contrast enhancement to the analyzer 12.

The analyzer 12 receives the first subtraction image data D21 and the image data D21a before contrast enhancement from the subtraction data generator 111. As illustrated in FIG. 2, the analyzer 12 specifies a region, where there is no blood flow, by a technique such as the analysis of voxel values, segmentation, or the like by using the image data D21a before contrast enhancement. The no blood-flow region may be, for example, a region corresponding to the air or a region corresponding to the bone. In the following, the specified region is sometimes referred to as "no blood-flow region". It is not necessary to determine image data to be analyzed in order to specify no blood-flow region. For example, the image data D21b after contrast enhancement may be used.

From among voxel data in the first difference image data D21, The analyzer 12 sets values of voxel data corresponding to no blood-flow region to zero on the first subtraction image data D21 to get image data D31. Although the term "voxel data" as used herein covers the value, the value is sometimes described as "the value of voxel data" when the value is emphasized in the explanation, when the value is used at the other processing, or the like. In this manner, the analyzer 12 removes the region that indicates no blood-flow region on the first subtraction image data D21. Incidentally, an example of "third image data" corresponds to image data created by removing no blood-flow region from the subtraction image data.

The analyzer 12 may normalize the value of third image data based on the value of voxel data corresponding to the arterial region on the third image data D31 to get image data D31'. In this case, the normalized third image data also corresponds to an example of "third image data".

The analyzer 12 may process the voxel values of third image data to get image data D31" so that minute blood vessels such as a capillary is relatively enhanced. The capillary region is a region of interest. As a specific example, the analyzer 12 sets a region indicating the artery (major blood vessel), that is, a part which has a high value of voxel data, to zero on third image data. Thus, the analyzer 12 removes the artery region from the third image data. In this case, the processed third image data also corresponds to an example of "third image data".

The analyzer 12 stores one or combinations of the third image data in the image data storage 20. Note that the third image data may have been normalized or processed. In addition, the analyzer 12 may store the image data D21a before contrast enhancement, the image data D21b after contrast enhancement and information of those processing.

The analyzer 12 performs the same processing for the first subtraction image data D21 to the first subtraction image data D22 that has been created based on projection data and the like after a procedure.

The registration processor 21 retrieves third image data (D31 and D32, D31' and D32', D31" and D32", or combinations) corresponding to before and after the procedure for comparison, and reconstruction data (D21a, D22a, . . . ) before contrast enhancement. It is hereinafter assumed that the registration processor 21 has retrieved the third image data D31 and the third image data D32, and the image data D21a and the image data D22a before contrast enhancement corresponding to the third image data, respectively. As described above, the third image data D31 and the image data D21a before contrast enhancement are image data related to the examination that is performed before a predetermined procedure. On the other hand, the third image data D32 and the image data D22a before contrast enhancement are image data related to the examination that is performed after the procedure.

The registration processor 21 extracts a rigid structure, whose shape does not change even if the subject moves, from the image data D21a and the image data D22a before contrast enhancement. The rigid structure may be, for example, an osseous structure or the like. Such rigid structure may be extracted, for example, based on the evaluation (e.g., threshold processing) of voxel data. The registration processor 21 allocates the image data D21a and the image data D22a before contrast enhancement by using the rigid structure. The registration processor 21 corrects misalignment between the third image data D31 and the third image data D32 based on misalignment information determined between the image data D21a and the image data D22a before contrast enhancement. Thus, the third image data D31 and D32 are corrected, and then the corrected third image data D31c and the corrected third image data D32c are gotten. In this registration, unique anatomical coordinate system of the third image data D31 and unique anatomical coordinate system of the third image data D32 are corrected based on the rigid structure.

The registration processor 21 sends the corrected third difference image data D31c and the corrected third image data D32c to the image processor 22.

The image processor 22 receives, from the registration processor 21, the corrected third image data D31c and the corrected third image data D32c. The image processor 22 adjusts (normalizes) the voxel data of either or both the corrected third image data D31c and the third image data D32c to get adjusted third image data D31v and D32v, respectively. For example, this correction is performed in the following manner: The image processor 22 corrects a predetermined voxel such that the voxel values of the third image data before and after a procedure match (indicate the same value) at the same position (the same anatomical position).

Incidentally, the region used at adjustment may be a region which is not affected by a treatment or the like. The reference region for adjustment may be specified by, for example, an operator (doctor, etc.) through the input unit (not illustrated).

In other words, the image processor 22 calculates an adjustment factor that makes the values of voxel data match between specified same anatomical region of third image data before and after a procedure. The image processor 22 adjusts, for example, the voxel values of all voxels of the third image data by using the correction factor. The image processor 22 may specify same region which has anatomically identical structure on the first subtraction image data D21 and D22, or the third image data. For example, the image processor 22 may specify the same region based on an automatic or semi-automatic processing technique such as segmentation, a comparison of the anatomical structure or comparison of structural information extracted from the anatomical structure.

As described above, the image processor 22 adjusts the voxel data of either or both the third image data so that the voxel values match in the same position (region) of them.

This adjustment is performed to generate second subtraction image data D41 (described later) which is obtained by subtracting the third image data before and after a procedure. Incidentally, the second subtraction image data D41 corresponds to an example of "fourth image data". Specifically, region which is affected by a procedure or the like is relatively enhanced by suppressing signals at specified region on the second subtraction image data D31. Accordingly, the above adjustment is performed to remove the specified region as much as possible so that the region can be negligible on the second subtraction image. Note that the subtraction between the third image data before and after a procedure corresponds to an example of "variation index".

The image processor 22 may automatically determine a correction factor. The region that is affected by a treatment or the like is a minor region in most cases. Based on this assumption, the image processor 22 statistically determines a correction factor so that voxel values agree at as many voxels as possible between the third image data before and after a procedure. In addition, the image processor 22 obtains the second subtraction image data D41 (the fourth image data) by subtracting the adjusted third image data before and after a procedure. As a result, regions which are not affected by treatment or the like disappear or become negligible, while regions which are affected by a treatment or the like are relatively enhanced.

Described below are two examples of the calculation of the adjustment factor by the image processor 22. In first example, the image processor 22 calculates an adjustment factor so that voxel data or small regions match (indicate the same value) at the same position (the same anatomical position) on the third image data before and after a procedure. Alternatively, in the first example, the image processor 22 calculates an adjustment factor so that voxel values of a plurality of small regions match at the same position on the third image data before and after a procedure. The average value of each small region is used as the voxel value at this time. The image processor 22 creates a histogram of adjustment factors, and determines an adjustment factor by determining a most frequent value from the histogram. The adjustment factor is applied to each region on the third image data. In second example, the image processor 22 determine adjustment factor so that negligible region which has less signals on the second subtraction image has maximum volume. As a result, the image processor 22 identifies an adjustment factor to maximize the volume H of voxel data or small regions that match each other at the same position (the same anatomical position) of two third image data. This may be obtained by deriving α to maximize the following equation:

$$H = \bigvee_{i=1}^{N} \{\alpha D31(x, y, z) - D32(x, y, z)\}^2 \qquad \text{[Equation 1]}$$

With respect to each small region i (i=1 to N) in the operator V, the image processor 22 checks the average value of $$\{\alpha D31(x,y,z) \cdot D32(x,y,z)\}^2$$

If the average value is within ±Δ, it is determined that they match each other, and the count is incremented by one. On the other hand, if the average value is not within ±Δ, it is not counted. By this operation of the image processor 22, it is possible to count the number of small regions, whose voxel values approximately match between the images, by changing the adjustment factor α gradually. The image processor 22 may determine the adjustment factor by searching maximum count of matched small regions.

The automatic adjustment factor (adjustment factor α) is calculated under the assumption that regions affected by a procedure, a treatment, or the like are minor. However, there are cases that do not conform to this assumption. As such cases, a state in which the adjustment factor α is far off from 1 is assumed. To cope with such a situation, for example, the image processor 22 determines whether the correction factor α falls within a range of 0.67 to 1.5. If the adjustment factor α is out of the range, the image processor 22 gives a notification (warning) to the operator. The notification may be provided as a visual or audio warning message. This notification may prompt the operator to specify a reference region for adjustment processing. In this case, the adjustment factor is determined based on the specified region.

After adjusting the voxel value of each voxel on the third image data before and after a procedure by adjustment factor α, as illustrated in FIG. 2, the image processor 22 generates the second subtraction image data D41 based on the subtraction between them. The second subtraction image data D41 thus generated can show, for example, a portion (e.g., improved or worsened part) that has been affected by a treatment or a procedure.

The image processor 22 performs image processing on the second subtraction image data D41 based on predetermined image processing conditions. For example, the image processor retrieves the image data D21a or D22a before contrast enhancement or the like. Then, the image processor 22 may superimpose the second subtraction image data D41 on the image data D21a or D22a before contrast enhancement to generate image data D42. In the example of FIG. 2, the image data D42 shows both anatomical structure and affected part simultaneously. With a medical image thus generated, for example, it is possible to identify a region that has changed since the examination corresponding to the first subtraction image data D21 until the examination corresponding to the first subtraction image data D22.

The image processor 22 retrieves the first subtraction image data D21 acquired before a procedure or the first subtraction image data D22 acquired after a procedure or the like. Further, the image processor 22 may generate another image data D42 by superimposing the second subtraction image data D31 on one of the first subtraction image data D21 or D22. In this manner, the image data D42 shows, for example, the positional relationship between an affected part (e.g., infarction) on the second subtraction image data D31 and major blood vessel (e.g., artery). At this time, image data on which capillary is enhanced by processing of voxel data are used instead of the first subtraction image data D21 or D22 for the other purpose.

The image processor 22 retrieves, for example, the image data D21b acquired after contrast enhancement and before a procedure or the like instead. Further, the image processor 22 may generate third example of fusion data by superimposing the second subtraction image data D31 on the image data D21b after contrast enhancement. The fusion image may be displayed in color. If the image processor 22 generates a image data in this manner, for example, the image data can show both the amount of blood flow at each part before a procedure and affected portion that has been affected by a procedure.

The image processor 22 sends the fusion image generated as above to the display controller 23. The display controller 23 receives the fusion image from the image processor 22, and displays it on the display 24.

Note that the image data storage 20 is only required to store image data for generating an image to be displayed on the display 24. Therefore, the image data storage 20 does not need to store the image data D21a, D22a, . . . before contrast enhancement and the image data D21b, D22b, . . . after contrast enhancement together with the first subtraction image data D21, D22 . . . . For example, if the image data is generated by using subtraction image data only, the image data storage 20 is required to store only the first subtraction image data D21, D22, . . . .

Figure 3:
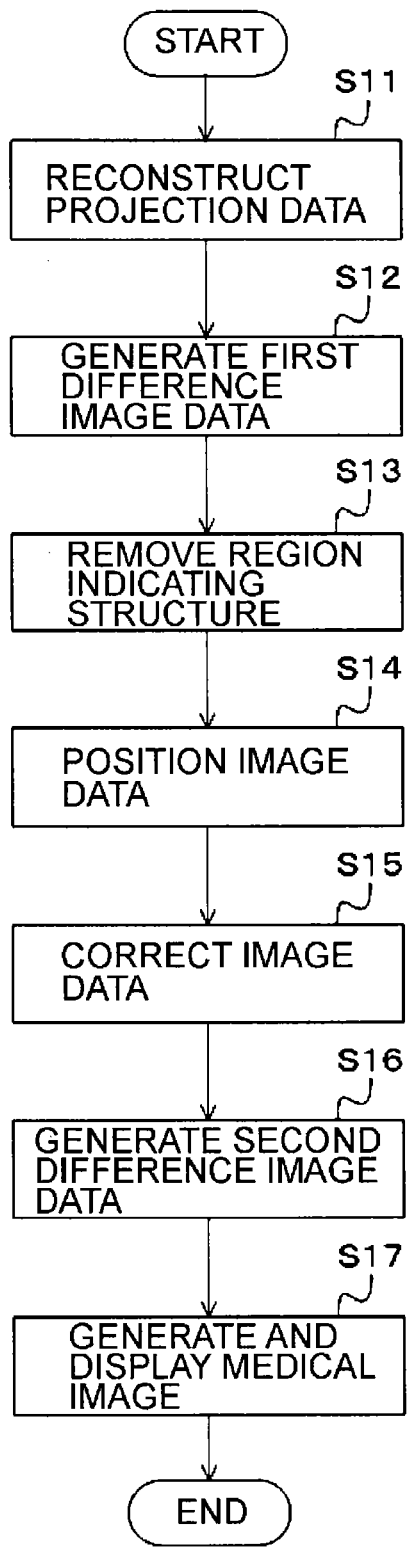
FIG. 3 is a flowchart of a series of the operation of the image processing apparatus of the embodiment.

Next, referring to FIG. 3, a description is given for explaining flowchart of the image processing apparatus 100 in this embodiment. Note that the following description is given for an example described above.

(Step S11)

The projection data storage 10 stores projection data acquired by the imaging unit 500 before and after a predetermined event, that is, the projection data D11a, D12a, . . . before contrast enhancement and the projection data D11b, D12b, . . . after contrast enhancement.

The reconstruction processor 11 retrieves the projection data, purpose of the acquisition in the examination, acquisition conditions such as acquisition before contrast enhancement or acquisition after contrast enhancement and acquisition time, from the projection data storage 10. The reconstruction processor 11 performs reconstruction processing to, for example, the projection data D11a and the projection data D11b acquired before a procedure.

By the reconstruction processing, the image data D21a before contrast enhancement and the image data D21b after contrast enhancement are generated. When retrieving the projection data D12a and D12b after the procedure, the reconstruction processor 11 performs the reconstruction processing to them to generate the image data D22a before contrast enhancement and the image data D22b after contrast enhancement.

The reconstruction processor 11 stores, in the image data storage 20, the image data D21a in association with the image data D21b after contrast enhancement, and the image data D22a in association with the image data D22b.

(Step S12)

Besides, the subtraction data generator 111 receives the image data before contrast enhancement and the image data after contrast enhancement from the reconstruction processor 11 in step S11, and obtains the subtraction data between them.

By obtaining the subtraction, the subtraction data generator 111 generates, for example, the first subtraction image data D21 that indicates the subtraction between the image data D21*a* before contrast enhancement and the image data D21*b* after contrast enhancement (see FIG. 2). The subtraction data generator 111 further generates the first subtraction image data D22 that indicates the subtraction between the image data D22*a* before contrast enhancement and the image data D22*b* after contrast enhancement.

The subtraction data generator 111 may obtain the subtraction between the projection data before contrast enhancement and that after contrast enhancement, and generate the subtraction image data by reconstructing the subtraction of the projection data.

(Step S13)

The subtraction data generator 111 sends at least one of the first subtraction image data D21 generated, the image data D21*a* before contrast enhancement, and the image data D21*b* after contrast enhancement to the analyzer 12. For example, the subtraction data generator 111 sends the first subtraction image data D21 and the image data D21*a* before contrast enhancement to the analyzer 12. Similarly, the subtraction data generator 111 sends the first subtraction image data D22 and the image data D22*a* before contrast enhancement to the analyzer 12.

The analyzer 12 receives the first subtraction image data D21 and the image data D21*a* before contrast enhancement from the subtraction data generator 111. The analyzer 12 specifies no blood-flow region in the image data D21*a* before contrast enhancement (see FIG. 2). The image data D21*b* after contrast enhancement may be used instead to specify no blood-flow region.

The analyzer 12 sets the value of voxel data corresponding to the no blood-flow region to zero. In this manner, the analyzer 12 removes the no blood-flow region from the first subtraction image data D21 to get image data D31.

The analyzer 12 may normalize the value of the subtraction image data D31 based on the values of voxel data corresponding to the arterial region.

In addition, the analyzer 12 may set the voxel value of, for example, a part indicating an artery with a high voxel value to zero in the image data D31 to relatively enhance minute blood vessels such as capillaries.

The analyzer 12 stores the image data D31 or the like in the image data storage 20. The analyzer 12 performs the same processing on the first difference image data D22 to get image data D32 or the like.

(Step S14)

The registration processor 21 retrieves the image data D31 (before a procedure) and the image data D32 (after the procedure), and also the image data D21*a* and the image data D22*a* before contrast enhancement corresponding to them, respectively.

The registration processor 21 extracts a rigid anatomical structure (bone, etc.), whose shape does not change even if the subject moves, from the image data D21*a* and the image data D22*a* before contrast enhancement by threshold processing or the like. The registration processor 21 allocates the image data D21*a* and the image data D22*a* before contrast enhancement by using extracted information. The registration processor 21 corrects the position and orientation of the image data D31 and the image data D32 based on allocation information between the image data D21*a* and D22*a* before contrast enhancement. Thus, the image data D31 and D32 are corrected.

The registration processor 21 sends the corrected image data D31*c* and the corrected image data D32*c*, to the image processor 22.

(Step S15)

The image processor 22 receives, from the registration processor 21, the corrected image data D31*c* and the corrected image data D32*c*. The image processor 22 adjusts either or both the corrected image data D31 and the corrected image data D32 so that voxel values match at the same region between the two image data D21 and D22. The same region which is not affected by a treatment is determined by the operator via the input unit (not illustrated), for example. The image processor 22 calculates an adjustment factor that makes the values of voxel data match between regions each specified on the corrected image data. The image processor 22 adjusts each voxel value of the corrected image data based on the adjustment factor.

First example or second example described above may be employed to automatically determine the adjustment factor.

(Step S16)

After adjusting each voxel value on the corrected image data D31*c* and the corrected image data D32*c*, the image processor 22 obtains the subtraction between these image data and thereby generates the second subtraction image data D31 (see FIG. 2).

(Step S17)

The image processor 22 performs image processing on the second subtraction image data D41 based on predetermined image processing conditions. For example, the image processor retrieves the image data D21*a* or D22*a* before contrast enhancement and before or after a procedure or the like used to generate the second subtraction image data D41. Then, the image processor 22 may superimpose the second subtraction image data D41 on the image data D21*a* or D22*a* before contrast enhancement to generate fusion image data D42. For example, in the example of FIG. 2, the fusion image data D32 is a schematic illustration of image data obtained by superimposing the second subtraction image data D41 on the image data D21*a* before contrast enhancement. The fusion image thus generated shows, for example, both improved or worsened region by a procedure and anatomical information simultaneously.

The image processor 22 may generate a fusion image by superimposing the second subtraction image data D41 on the first subtraction image data D21 or D22. At this time, fusion image shows relationship between affected region and major blood vessels.

The image processor 22 may generate a fusion image displayed in color by superimposing the second subtraction image data D41 on the image data D21*b* after contrast enhancement.

The image processor 22 sends the fusion image generated in the above manner to the display controller 23. The display controller 23 receives the fusion image from the image processor 22, and displays it on the display 24.

As described above, the image processing apparatus 100 of this embodiment generates subtraction image data indicating affected region by a procedure. With this configuration of the image processing apparatus 100 of the embodiment, an affected part, which has newly developed from before to after a predetermined event such as a procedure, can be displayed with additional information by fusing the anatomical information such as osseous or vessel structures.

(Modification)

The image processing apparatus 100 of the embodiment is described above as obtaining the subtraction between the first subtraction image data between image data before and after a procedure or the like (D31 and D32, an example of "third image data"), and thus generating the second subtraction image data D41 (an example of "fourth image data"). However, the embodiment is not limited to this and may be constructed as follows, for example.

After correcting the voxel value of each voxel in the corrected image data D31c acquired prior to a procedure and the first corrected image data D32c acquired after the procedure, the image processor 22 divides the image data D32 by the image data D31. A specific example is represented by the following equation, where PB (x, y, z) is the corrected image data D31c before a procedure, and PA (x, y, z) is the corrected image data D32c after the procedure.

$$\frac{PA(x, y, z)}{PB(x, y, z)} \quad \text{[Equation 2]}$$

The image processor 22 generates the second subtraction image data D41 by the division of these image data.

Incidentally, there are cases where the value of PB (x, y, z) in the above equation is approximately zero. In such a case, the subtraction value may be close to infinite number. Accordingly, when the value of PB (x, y, z) is close to zero, the image processor 22 adds a predetermined constant to PB (x, y, z), and then divides the corrected image data D32c by the corrected image data D31c. A specific example is represented by the following equation, where "k" indicates the constant.

$$\frac{PA(x, y, z)}{PB(x, y, z) + k} \quad \text{[Equation 3]}$$

Incidentally, the result of dividing the corrected image data D32c by the corrected image data D31c corresponds to an example of "variation index".

In this modification, as in the embodiment described above, the image processing apparatus 100 generates subtraction image data indicating affected region by a procedure. Further, the image processing apparatus 100 divides the corrected image data after the predetermined event by the corrected image data before the predetermined event. The image processing apparatus 100 of the modification displays a fusion image generated based on this division or subtraction on the display 24. With this configuration of the image processing apparatus 100 also, an affected part, which has newly developed from before to after a predetermined event such as a procedure, can be displayed in a manner recognizable by the viewer of the image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus, comprising
a display; and
processing circuitry configured to
generate second image data by subtracting first image data after contrast enhancement from first image data before contrast enhancement,
remove information indicating a structure from a plurality of the second image data to generate third image data,
correct misalignment of a plurality of the third image data based on characteristics of shape of a subject represented in at least any one of the first image data, the second image data, and the third image data,
obtain a variation index between the third image data after alignment correction, and generate fourth image data base on the variation index, and
display a medical image based on the fourth image data on the display.

2. The image processing apparatus of claim 1, wherein the processing circuitry is further configured to
generate the second image data based on the first image data before contrast enhancement and the first image data after contrast enhancement acquired before a predetermined event,
generate the second image data based on the first image data before contrast enhancement and the first image data after contrast enhancement acquired after the predetermined event, and
correct misalignment of the third image data before the predetermined event and the third image data after the predetermined event.

3. The image processing apparatus of claim 2, wherein the predetermined event includes procedure, therapy, or treatment for the subject.

4. The image processing apparatus of claim 2, wherein the processing circuitry is further configured to obtain a difference between the third image data as the variation index after misalignment correction, and generate the fourth image data base on the difference.

5. The image processing apparatus of claim 4, wherein the processing circuitry is further configured to divide the third image data before the predetermined event by the third image data after the predetermined event, and generate the fourth image data base on a result of division as the variation index.

6. The image processing apparatus of claim 5, wherein the processing circuitry is further configured to add a predetermined constant to the third image data before the predetermined event or the third image data after the predetermined event prior to the division.

7. The image processing apparatus of claim 1, wherein the processing circuitry is further configured to specify the characteristics of the shape in at least either one of the first image data before contrast enhancement and the first image data after contrast enhancement.

8. The image processing apparatus of claim 7, wherein the processing circuitry is further configured to specify the characteristics of the shape from a region corresponding to a bone or a region corresponding to air in the first image data before contrast enhancement or the first image data after contrast enhancement.

9. The image processing apparatus of claim 1, wherein the processing circuitry is further configured to
adjust voxel values of the third image data such that voxel values match between anatomically identical regions of the subject in the third image data, and obtain the variation index between the third image data after adjustment.

10. The image processing apparatus of claim 1, wherein the processing circuitry is further configured to
adjust voxel values of the third image data such that voxel values match between the third image data based on a region specified through an input circuit, and
obtain the variation index between of the third image data after adjustment.

11. The image processing apparatus of claim 9, wherein
the voxel values are average values of the voxel values in the anatomically identical regions of the subject, and
the processing circuitry is further configured to calculate an adjustment factor based on the third image data before obtaining the variation index to achieve a largest regions in which the average values match between the third image data.

12. The image processing apparatus of claim 11, wherein the processing circuitry is further configured to, when the adjustment factor falls out of a predetermined range, stop calculation of the adjustment factor and output a warning.

13. The image processing apparatus of claim 2, wherein the processing circuitry is further configured to display the medical image on the display based on the first image data before contrast enhancement and the fourth image data.

14. The image processing apparatus of claim 2, wherein the processing circuitry is further configured to display the medical image on the display based on the second image data and the fourth image data.

15. The image processing apparatus of claim 2, wherein the processing circuitry is further configured to display the medical image on the display based on the first image data after contrast enhancement and the fourth image data.

16. The image processing apparatus of claim 15, wherein the processing circuitry is further configured to display the medical image obtained by superimposing the fourth image data on the first image data on the display.

17. The image processing apparatus of claim 14, wherein the processing circuitry is further configured to display the medical image obtained by superimposing the fourth image data on the second image data on the display.

18. An image processing method, comprising:
generating second image data indicating a difference between first image data before contrast enhancement and first image data after contrast enhancement, the first image data being acquired by capturing an image of a subject at different times,
removing information indicating a structure from a plurality of the second image data corresponding to the different times to generate third image data,
correcting misalignment of a plurality of the third image data based on characteristics of shape of the subject represented in at least any one of the first image data, the second image data, and the third image data,
obtaining a variation index between the third image data after misalignment correction, and generating fourth image data base on the variation index, and
displaying a medical image based on the fourth image data on a display.

19. The image processing method of claim 18, wherein the generating includes
generating the second image data based on the first image data before contrast enhancement and the first image data after contrast enhancement acquired before a predetermined event, and
generating the second image data based on the first image data before contrast enhancement and the first image data after contrast enhancement acquired after the predetermined event, and
the correcting includes correcting the misalignment of the third image data before the predetermined event and the third image data after the predetermined event.

* * * * *